United States Patent
Hsieh et al.

(10) Patent No.: US 11,135,164 B2
(45) Date of Patent: *Oct. 5, 2021

(54) RELOADABLE HYDROGEL SYSTEM COMPRISING AN ANTI-PEG ANTIBODY FOR TREATING MYOCARDIAL INFARCTION

(71) Applicant: Academia Sinicia, Taipei (TW)

(72) Inventors: Patrick C. H. Hsieh, Taichung (TW); David Lundy, Taipei (TW); Christopher Yu-Tai Yen, Taipei (TW)

(73) Assignee: ACADEMIA SINICA, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 16/477,567

(22) PCT Filed: Jan. 12, 2018

(86) PCT No.: PCT/EP2018/050778
§ 371 (c)(1),
(2) Date: Jul. 12, 2019

(87) PCT Pub. No.: WO2018/130660
PCT Pub. Date: Jul. 19, 2018

(65) Prior Publication Data
US 2020/0121596 A1 Apr. 23, 2020

Related U.S. Application Data

(60) Provisional application No. 62/445,791, filed on Jan. 13, 2017.

(51) Int. Cl.
| | |
|---|---|
| C07K 16/44 | (2006.01) |
| A61K 9/06 | (2006.01) |
| A61K 39/395 | (2006.01) |
| A61K 38/18 | (2006.01) |
| A61K 38/19 | (2006.01) |
| A61K 47/60 | (2017.01) |
| A61P 9/10 | (2006.01) |
| A61P 9/06 | (2006.01) |
| A61K 38/30 | (2006.01) |
| C07K 14/475 | (2006.01) |
| C07K 14/485 | (2006.01) |
| C07K 14/49 | (2006.01) |
| C07K 14/495 | (2006.01) |
| C07K 14/50 | (2006.01) |
| C07K 14/505 | (2006.01) |
| C07K 14/52 | (2006.01) |
| C07K 14/535 | (2006.01) |
| A61K 47/36 | (2006.01) |
| C07K 14/65 | (2006.01) |

(52) U.S. Cl.
CPC ............ *A61K 9/06* (2013.01); *A61K 38/18* (2013.01); *A61K 38/185* (2013.01); *A61K 38/1816* (2013.01); *A61K 38/1825* (2013.01); *A61K 38/1833* (2013.01); *A61K 38/1841* (2013.01); *A61K 38/1858* (2013.01); *A61K 38/1866* (2013.01); *A61K 38/1883* (2013.01); *A61K 38/193* (2013.01); *A61K 38/30* (2013.01); *A61K 39/3955* (2013.01); *A61K 47/60* (2017.08); *A61P 9/10* (2018.01); *C07K 16/44* (2013.01); *A61K 47/36* (2013.01); *C07K 14/475* (2013.01); *C07K 14/4753* (2013.01); *C07K 14/4756* (2013.01); *C07K 14/49* (2013.01); *C07K 14/495* (2013.01); *C07K 14/50* (2013.01); *C07K 14/505* (2013.01); *C07K 14/535* (2013.01); *C07K 14/65* (2013.01)

(58) Field of Classification Search
CPC ........ C07K 16/44; C07K 14/535; A61K 9/06; A61K 38/193; A61P 9/10
See application file for complete search history.

(56) References Cited

U.S. PATENT DOCUMENTS 10,532,097 B2 * 1/2020 Hsieh ................. C07K 16/44

FOREIGN PATENT DOCUMENTS

| WO | 2016/007856 A1 | 1/2016 |
| WO | 2016007856 A1 | 1/2016 |

OTHER PUBLICATIONS

Kozma etal, 2020, Advanced Drug Delivery Reviews, pp. 1-13.*
Jasmine, P.J. Wu, et al.; "Reloadable multidrug capturing delivery system for targeted ischemic disease treatment"; Science Translational Medicine; vol. 8, No. 365; Nov. 16, 2016; pp. 1-13.
Jianyu, Li, et al.; :Designing hydrogels for controlled drug delivery; Nature Reviews Materials; vol. 1, No. 12; Oct. 18, 2016; pp. 1-38.
PCT/EP2018/050778, Apr. 9, 2019, International Search Report and Written Opinion*.
Su, et al., "Sensitive Quantification of PEGylated Compounds by Second-Generation Anti-Poly(ethylene glycol) Monoclonal Antibodies", Bioconjugate Chem. 2010, 21, 1264-1270, 7 pages.

* cited by examiner

*Primary Examiner* — Zachary C Howard
(74) *Attorney, Agent, or Firm* — Polsinelli PC; Ron Galant (57) ABSTRACT

A drug delivery system and methods of using such for delivering a peglyated therapeutic agent to heart. The drug delivery system may comprise an antibody embedded in a hydrogel, comprising one or more biodegradable polymers, up to about 60% of which contain inter-chain or intra-chain covalent crosslinks.

16 Claims, 5 Drawing Sheets

Sham

I/R

HA/IgM

HA/Anti-PEG

Figure 3

RELOADABLE HYDROGEL SYSTEM COMPRISING AN ANTI-PEG ANTIBODY FOR TREATING MYOCARDIAL INFARCTION

CROSS-REFERENCE TO RELATED APPLICATIONS

The present application is a national stage filing under 35 U.S.C. § 371 of PCT International Application No. PCT/EP2018/050778, filed Jan. 12, 2018, which claims priority under 35 U.S.C. § 119(e) to U.S. Provisional Application No. 62/445,791, entitled "RELOADABLE HYDROGEL SYSTEM FOR TREATING MYOCARDIAL INFARCTION," filed Jan. 13, 2017, the entire contents of each of which are incorporated by reference herein in their entirety.

BACKGROUND OF THE INVENTION

Delivery of therapeutic agents to heart for treating myocardial infarction could be challenging due to various factors. Heart contains densely packed myocardium with highly ordered arrangement. Constant contraction due to the beating of the heart is likely to accelerate loss of therapeutic agents. Further, upon occurrence of an ischemic event, the majority of the infarction area in the myocardium becomes isolated from the vasculature with just the border zone in contact with healthy myocardium. Thus, the damaged regions may be isolated from circulation as there will be fewer points of secondary circulation. This would hamper delivery of therapeutic agents to the damaged regions.

It is therefore important to develop new and efficient drug delivery systems for delivering therapeutic agent to heart, particularly ischemic areas in the heart, for treating heart diseases.

SUMMARY OF THE INVENTION

The present disclosure is based, at least in part, on the development of a hydrogel-based drug delivery system comprising antibodies capable of attracting therapeutic agents to heart.

In one aspect, provided herein is a drug delivery system for delivering a therapeutic agent to heart, comprising an antibody (e.g., an IgG or IgM immunoglobulin molecule) embedded in a hydrogel, wherein the hydrogel comprises one or more biodegradable polymers, up to about 60% (e.g., about 25% to about 50%) of which contain inter-chain or intra-chain covalent crosslinks, wherein the antibody binds polyethylene glycol (PEG). In some instances, the amount of the antibody in the drug delivery system is about 0.5-1% (w/v).

In some embodiments, the hydrogel comprises hyaluronic acid (HA) molecules. Alternatively or in addition, the antibody for use in making the drug delivery system described herein may specifically binds PEG having a specific range of molecular weights. In some embodiments, the antibody is a human antibody or a humanized antibody.

In another aspect, provided herein is a kit for delivering a therapeutic agent to heart, comprising: (i) any drug delivery systems as described herein; and (ii) a therapeutic agent for treating a heart disease, wherein the therapeutic agent is conjugated to polyethylene glycol (PEG). The therapeutic agent can be a drug for treating a heart disease (e.g., an ischemic heart disease such as myocardial infarction), for example, a growth factor. Examples include, but are not limited to, insulin-like growth factor, granulocyte-colony stimulating factor (G-CSF), erythropoietin, a vascular endothelial growth factor, a platelet-derived growth factor, a hepatocyte growth factor, a neuregulin, a neurotrophin, a fibroblast growth factor, a stromal cell-derived factor, a growth differentiation factor, a transforming growth factor, a glial cell-derived neurotrophic factor, a migration stimulating factor, and a macrophage stimulating factor.

In yet another aspect, provided herein is a method for delivering a therapeutic agent to heart, comprising: (i) administering to a subject having or at risk for heart ischemia any of the drug delivery systems described herein, wherein the drug delivery system is placed at a heart area where a heart disorder (e.g., heart ischemia or myocardial infarction) occurs or is suspected to occur; and (ii) administering systemically a therapeutic agent for treating a heart disorder such as heart ischemia or myocardial infarction, wherein the therapeutic agent is conjugated with polyethylene glycol (PEG). In some instances, about 1-2 ml of the drug delivery system is administered to the subject each time. The drug delivery system may be administered to the subject by multiple doses. Alternatively, the drug delivery system may be administered to the subject only once.

Also within the scope of the present disclosure are hydrogels embedded with an anti-PEG antibody as described herein for use in delivery of therapeutic agents to a heart area and treat a heart disorder as described herein when co-used with a pegylated therapeutic agent for treating the heart disorder. Also provided herein are uses of the drug delivery system as described herein (together with a pegylated therapeutic agent) in manufacturing a medicament in use for the asserted purpose.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

FIG. 2 includes diagrams showing the successful delivery of agents to heart using an exemplary drug delivery system as described herein. A: IVIS image showing PEG-modified quantum dot accumulation in mouse hearts following ischemia-reperfusion injury. B: Quantification of PEG-modified quantum dot accumulation (n=6 per group). C: photo and chart showing linearity of IVIS measurement. D: Histological analysis of cardiac tissue shows increased PEG-modified quantum dots (red) in the border zone of the infarct-damaged left ventricle (cardiac troponin I, green) following use of the HA/anti-PEG capture system. Sham=sham surgery only. I/R=ischemia-reperfusion surgery followed by systemic quantum dot administration. HA/IgM, HA/anti-PEG reflect the intracardiac injections performed, followed by systemic quantum dot administration.

DETAILED DESCRIPTION OF THE INVENTION

Due to the different physiology conditions in different organs, different drug delivery systems may be needed to enhance delivery efficiency and retention time of therapeutic agents for treating diseases associated with particular organs, for example, myocardial infarction.

In the case of treating myocardial infarction vs. limb ischemia, whilst both the myocardium and skeletal muscle are highly vascularized, striated muscle, the physiological differences between these two muscles represents a different biophysical environment—operating the depot for the myocardium is considerably more challenging. Not only is the myocardium denser and arranged differently to skeletal muscle, there is a constant contraction due to the beating of the heart. Furthermore, upon the occurrence of an ischemic event, the majority of the infarct area in the myocardium becomes isolated from the vasculature with just the border zone in contact with healthy myocardium. This could hamper delivery of therapeutic agent to the ischemic areas due to the lack of circulation.

Such physiological and biophysical differences therefore present a distinct challenge in configuring the aforementioned drug delivery system to deliver the highest therapeutic benefit for heart diseases, such as myocardial infarction. Further, local injection of therapeutic agents in a heart area was found to be ineffective because of the quick loss of the therapeutic agent.

The present disclosure provides improved drug delivery systems to enhance drug delivery efficiency to heart and/or to prolong drug retention at heart areas. The drug delivery systems described herein comprises hydrogels embedded with a suitable anti-PEG antibody. Features of such a drug delivery system, for example, the type of biodegradable polymer(s) used in the hydrogel, the content of crosslinking therein, features of the anti-PEG antibody, the amount of the antibody in the drug delivery system as relative to the hydrogel, etc., are designed such that the drug delivery systems are particularly suitable for delivering therapeutic agents to heart.

For example, the drug delivery system contains biodegradable polymer(s) having a suitable cross-linking level (e.g., up to about 60%). It was observed unexpected that a higher cross-linking level of biodegradable polymers such as hyaluronic acids led to lower antibody retention while lower levels of cross-linking led to higher antibody retention.

The drug delivery systems described herein could be used effectively in delivering pegylated therapeutic agents to heart and prolong the retention of the therapeutic agents in the heart areas, thereby benefiting treatment of heart disorders such as myocardial infarction.

Hydrogel-Based Drug Delivery System

The hydrogel-based drug delivery system described herein comprises one or more biodegradable polymers forming a matrix structure, in which an antibody capable of binding to polyethylene glycol (PEG) is embedded.

(i) Hydrogels

The hydrogel for use in the drug delivery system described herein can be a network formed by at least hydrophilic polymer(s). In some instances, the hydrogel can be in the form of colloidal gel containing water as the dispersion medium. In some examples, the hydrogel may contain greater than 50% (e.g., 50%, 60%, 70%, 80%, or 90%) water. Due to the high water content, hydrogels may possess a certain degree of flexibility similar to natural tissue.

The hydrogels for use in the drug delivery system described herein may comprise one or more biodegradable polymers, either naturally-occurring or synthetic (non-naturally occurring). Alternatively, the polymers may contain a certain level of intra-chain and/or inter-chain crosslinks, for example, up to about 60%, up to about 50%, up to about 40%, up to about 30%, up to about 25%, or up to about 20%. In one example, about 25% to about 50% of the polymers in the hydrogel contain inter-chain and/or intra-chain crosslinks. As used herein, "crosslink" refers to one or more bonds that link one polymer chain to another. Such bonds can be covalent bonds or ionic bonds.

In some embodiments, the hydrogel comprises one or more naturally occurring biodegradable polymers, for example, hyaluronan (also known as hyaluronic acid or HA) or a derivative of HA, collagen, gelatin, fibronectin, fibrinogen, alginate, chitosan, a fibrin glue made of fibrinogen and thrombin.

HA is a polymer of disaccharide units each composed of D-glucuronic acid and D-N-acetylglucosamine, which are linked via alternating $\beta$1,4- and $\beta$1,3-glycosidic bonds. HA has been found to play various physiological roles in the intercellular matrix, including cell migration, proliferation, and differentiation, tissue repair and hydrodynamics, and immune regulation. Naturally-occurring HA often contains 10,000 or more of the disaccharide units, the molecular weight of which can reach 4 million daltons or higher. Such high molecular weight HA molecules can be degraded via enzymatic, chemical, or physical methods to produce depolymerized HA products. The HA molecules for use in making the drug delivery system described herein may have a suitable molecular weight range, for example, about 20 kDa to about 200 kDa, about 50 kDa to about 100 kDa, about 100 kDa to about 200 kDa, about 200 kDa to about 300 kDa, about 200 kDa to about 500 kDa, about 300 kDa to about 400 kDa, about 500 kDa to about 1,000 kDa, about 800 kDa to about 1,000 kDa, about 1,000 kDa to about 2,000 kDa, about 1,000 kDa to about 1,500 kDa, about 1,500 kDa to about 2,000 kDa, about 2,000 kDa to about 5,000 kDa, and about 5,000 kDa to about 10,000 kDa. In particular examples, the HA molecules used for making the drug delivery system described herein may have a molecular weight ranging from about 50 kDa to about 75 kDa (for example, having an average MW of 60 kDa).

Derivatives of hyaluronic acid include, but are not limited to, partial or total esters of hyaluronic acid, adipic dihydrazide-modified hyaluronan, amides of hyaluronan, crosslinked hyaluronic acid, heavy metal salts of hyaluronic acid, sulphated hyaluronic acid, N-sulphated hyaluronic acid, amine-modified hyaluronic acid, diamine-modified hyaluronic acid, and hyaluronan composites such as composites of hyaluronan and silk, and hyaluronic acids cross-linked with other natural or synthetic materials. Derivatives of hyaluronic acid can be obtained by chemically modifying one or more functional groups (e.g., carboxylic acid group, hydroxyl group, reducing end group, N-acetyl group) of hyaluronic acid and/or crosslinking hyaluronan with other molecules using methods known in the art.

In some examples, the hydrogel is the fibrin glue, which is made up of fibrinogen and thrombin, wherein the thrombin is known to convert the fibrinogen therein into fibrin monomers in a relatively short period of time (e.g., 10 to 60 seconds), thereby giving rise to a three-dimensional gel like structure.

In other embodiments, the hydrogel may comprise one or more synthetic polymers, which may be selected from the group consisting of, poly(glycolic acid) (PGA), poly(lactic acid) (PLA), polyurethane (PU), poly(E-caprolactone) (PCL), polyvinyl alcohol) (PVA), polycyanoacrylate (PCA), polyacrylamide, polymethylmethacrylate, (PMMA), poly (lactide-co-glycolide) (PLGA), poly(trimethylene carbonate) (PTMC), polydimethylsiloxane (PDMS), poly(ethylene-co-vinylacetate) (PEVA), poly(glycolide-co-caprolactone) (PGCL), and poly(lactide-co-caprolactone) (PLCL).

In some embodiments, the hydrogel may comprise a combination of naturally-occurring polymers and synthetic polymers. Other information about suitable hydrogels for use in the drug delivery system described herein can be found in WO2016/007856, the relevant disclosures therein are incorporated by reference.

(ii) Anti-PEG Antibodies

The antibody for use in the drug delivery systems described herein is capable of binding to PEG. An antibody (interchangeably used in plural form) is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term "antibody" encompasses not only intact (i.e., full-length) polyclonal or monoclonal antibodies, but also antigen-binding fragments thereof (such as Fab, Fab', F(ab')2, Fv), single chain (scFv), mutants thereof, fusion proteins comprising an antibody portion, humanized antibodies, chimeric antibodies, diabodies, nanobodies, linear antibodies, single chain antibodies, multispecific antibodies (e.g., bispecific antibodies) and any other modified configuration of the immunoglobulin molecule that comprises an antigen recognition site of the required specificity, including glycosylation variants of antibodies, amino acid sequence variants of antibodies, and covalently modified antibodies. An antibody includes an antibody of any class, such as IgD, IgE, IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

The anti-PEG antibody used herein may specifically or preferentially bind PEG having a certain molecular weight range. An antibody that "specifically binds" to an antigen or an epitope is a term well understood in the art. A molecule is said to exhibit "specific binding" if it reacts more frequently, more rapidly, with greater duration and/or with greater affinity with a particular target antigen than it does with alternative targets. An antibody "specifically binds" to PEG having a specific molecular weight a if it binds with greater affinity, avidity, more readily, and/or with greater duration than it binds to PEG having a different molecular weight. It is also understood with this definition that, for example, an antibody that specifically binds to PEG having a specific molecular weight may or may not specifically or preferentially bind to PEG having a different molecular weight. As such, "specific binding" or "preferential binding" does not necessarily require (although it can include) exclusive binding. In some examples, an antibody that "specifically binds" to PEG having a specific molecular weight may not bind to PEG having a different molecular weight.

In some embodiments, the anti-PEG antibody (which may be an IgG or IgM molecule) may specifically bind to PEG having a high molecular weight (e.g., having a molecular weight greater than 10,000 kDa, for example, 15,000 kDa, 20,000 kDa, 25,000 kDa, 30,000 kDa or higher)) as compared with PEG having a low molecular weight (e.g., lower than 5,000 kDa, e.g., 3,000 kDa, 2,000 kDa, 1,000 kDa, 500 kDa, or lower). Selection of an anti-PEG antibody having specific binding activity to PEG having a specific molecular weight would depend on the molecular weight of PEG conjugated to a target therapeutic agent. For example, if a target therapeutic agent to be delivered to heart is conjugated with PEG having a high molecular weight, the anti-PEG antibody used in the drug delivery system is preferred to have a specific binding activity to high molecular weight PEG. Alternatively, if a target therapeutic agent to be delivered to heart is conjugated with PEG having a low molecular weight, the anti-PEG antibody used in the drug delivery system is preferred to have a specific binding activity to low molecular weight PEG.

Alternatively or in addition, an anti-PEG antibody as described herein has a suitable binding affinity for PEG, e.g., PEG having a specific molecular weight. As used herein, "binding affinity" refers to the apparent association constant or $K_A$. The $K_A$ is the reciprocal of the dissociation constant ($K_D$). The anti-PEG antibody described herein may have a binding affinity ($K_D$) of at least $10^{-5}$, $10^{-6}$, $10^{-7}$, $10^{-8}$, $10^{-9}$, $10^{-10}$ M, or lower for the target antigen or antigenic epitope. An increased binding affinity corresponds to a decreased $K_D$. Higher affinity binding of an antibody for a first antigen relative to a second antigen can be indicated by a higher $K_A$ (or a smaller numerical value $K_D$) for binding the first antigen than the $K_A$ (or numerical value $K_D$) for binding the second antigen. In such cases, the antibody has specificity for the first antigen (e.g., a first protein in a first conformation or mimic thereof) relative to the second antigen (e.g., the same first protein in a second conformation or mimic thereof; or a second protein). In some embodiments, the anti-PEG antibodies described herein have a higher binding affinity (a higher $K_A$ or smaller $K_D$) to PEG having a specific molecular weight as compared to the binding affinity to PEG having a different molecular weight. Differences in binding affinity (e.g., for specificity or other comparisons) can be at least 1.5, 2, 3, 4, 5, 10, 15, 20, 37.5, 50, 70, 80, 91, 100, 500, 1000, 10,000 or $10^5$ fold. In some embodiments, any of the anti-PEG antibodies may be further affinity matured to increase the binding affinity of the antibody to PEG, for example, PEG having a specific molecular weight.

Binding affinity (or binding specificity) can be determined by a variety of methods including equilibrium dialysis, equilibrium binding, gel filtration, ELISA, surface plasmon resonance, or spectroscopy (e.g., using a fluorescence assay). Exemplary conditions for evaluating binding affinity are in HBS-P buffer (10 mM HEPES pH7.4, 150 mM NaCl, 0.005% (v/v) Surfactant P20). These techniques can be used to measure the concentration of bound binding protein as a function of target protein concentration. The concentration of bound binding protein ([Bound]) is generally related to the concentration of free target protein ([Free]) by the following equation:

$$[Bound]=[Free]/(Kd+[Free])$$

It is not always necessary to make an exact determination of $K_A$, though, since sometimes it is sufficient to obtain a quantitative measurement of affinity, e.g., determined using a method such as ELISA or FACS analysis, is proportional to $K_A$, and thus can be used for comparisons, such as determining whether a higher affinity is, e.g., 2-fold higher, to obtain a qualitative measurement of affinity, or to obtain an inference of affinity, e.g., by activity in a functional assay, e.g., an in vitro or in vivo assay.

Antibodies capable of binding PEG as described herein can be made by any method known in the art. See, for example, Harlow and Lane, (1998) Antibodies: A Laboratory Manual, Cold Spring Harbor Laboratory, New York.

In some embodiments, antibodies specific to PEG, for example, PEG with a specific molecular weight, can be made by the conventional hybridoma technology. The PEG antigen, optionally coupled to a carrier protein such as KLH, can be used to immunize a host animal for generating antibodies binding to that antigen. The route and schedule of immunization of the host animal are generally in keeping with established and conventional techniques for antibody stimulation and production, as further described herein. General techniques for production of mouse, humanized, and human antibodies are known in the art and are described herein. It is contemplated that any mammalian subject including humans or antibody producing cells therefrom can be manipulated to serve as the basis for production of mammalian, including human hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C. (1975) Nature 256:495-497 or as modified by Buck, D. W., et al., In Vitro, 18:377-381 (1982). Available myeloma lines, including but not limited to X63-Ag8.653 and those from the Salk Institute, Cell Distribution Center, San Diego, Calif., USA, may be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBV immortalized B cells may be used to produce the anti-PEG monoclonal antibodies described herein. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that produce anti-PEG antibodies may be grown in vitro or in vivo using known procedures. The monoclonal antibodies may be isolated from the culture media or body fluids, by conventional immunoglobulin purification procedures such as ammonium sulfate precipitation, gel electrophoresis, dialysis, chromatography, and ultrafiltration, if desired. Undesired activity if present, can be removed, for example, by running the preparation over adsorbents made of the immunogen attached to a solid phase and eluting or releasing the desired antibodies off the immunogen. Immunization of a host animal with a target antigen or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example maleimidobenzoyl sulfosuccinimide ester (conjugation through cysteine residues), N-hydroxysuccinimide (through lysine residues), glutaraldehyde, succinic anhydride, $SOCl$, or $R1N=C=NR$, where R and R1 are different alkyl groups, can yield a population of antibodies (e.g., monoclonal antibodies).

If desired, an antibody (monoclonal or polyclonal) of interest (e.g., produced by a hybridoma) may be sequenced and the polynucleotide sequence may then be cloned into a vector for expression or propagation. The sequence encoding the antibody of interest may be maintained in vector in a host cell and the host cell can then be expanded and frozen for future use. In an alternative, the polynucleotide sequence may be used for genetic manipulation to "humanize" the antibody or to improve the affinity (affinity maturation), or other characteristics of the antibody.

In other embodiments, fully human antibodies can be obtained by using commercially available mice that have been engineered to express specific human immunoglobulin proteins. Transgenic animals that are designed to produce a more desirable (e.g., fully human antibodies) or more robust immune response may also be used for generation of humanized or human antibodies. Examples of such technology are Xenomouse® from Amgen, Inc. (Fremont, Calif.) and HuMAb-Mouse® and TC Mouse™ from Medarex, Inc. (Princeton, N.J.). In another alternative, antibodies may be made recombinantly by phage display or yeast technology. See, for example, U.S. Pat. Nos. 5,565,332; 5,580,717; 5,733,743; and 6,265,150; and Winter et al., (1994) Annu. Rev. Immunol. 12:433-455. Alternatively, the phage display technology (McCafferty et al., (1990) Nature 348:552-553) can be used to produce human antibodies and antibody fragments in vitro, from immunoglobulin variable (V) domain gene repertoires from unimmunized donors.

Alternatively, antibodies capable of binding to the PEG antigens as described herein may be isolated from a suitable antibody library via routine practice. Antibody libraries, which contain a plurality of antibody components, can be used to identify antibodies that bind to a specific target antigen (e.g., a PEG molecule having a certain molecular weight) following routine selection processes as known in the art. In the selection process, an antibody library can be probed with the target PEG antigen and members of the library that are capable of binding to the target PEG antigen can be isolated, typically by retention on a support. Such screening process may be performed by multiple rounds (e.g., including both positive and negative selections) to enrich the pool of antibodies capable of binding to the target PEG antigen. Individual clones of the enriched pool can then be isolated and further characterized to identify those having desired binding activity and biological activity. Sequences of the heavy chain and light chain variable domains can also be determined via conventional methodology.

There are a number of routine methods known in the art to identify and isolate antibodies capable of binding to the target PEG antigens described herein, including phage display, yeast display, ribosomal display, or mammalian display technology.

As an example, phage displays typically use a covalent linkage to bind the protein (e.g., antibody) component to a bacteriophage coat protein. The linkage results from translation of a nucleic acid encoding the antibody component fused to the coat protein. The linkage can include a flexible peptide linker, a protease site, or an amino acid incorporated as a result of suppression of a stop codon. Phage display is described, for example, in U.S. Pat. No. 5,223,409; Smith (1985) *Science* 228:1315-1317; WO 92/18619; WO 91/17271; WO 92/20791; WO 92/15679; WO 93/01288; WO 92/01047; WO 92/09690; WO 90/02809; de Haard et al. (1999) *J. Biol. Chem* 274:18218-30; Hoogenboom et al.

(1998) *Immunotechnology* 4:1-20; Hoogenboom et al. (2000) *Immunol Today* 2:371-8 and Hoet et al. (2005) *Nat Biotechnol.* 23(3)344-8. Bacteriophage displaying the protein component can be grown and harvested using standard phage preparatory methods, e.g. PEG precipitation from growth media. After selection of individual display phages, the nucleic acid encoding the selected protein components can be isolated from cells infected with the selected phages or from the phage themselves, after amplification. Individual colonies or plaques can be selected, and then the nucleic acid may be isolated and sequenced.

Other display formats include cell-based display (see, e.g., WO 03/029456), protein-nucleic acid fusions (see, e.g., U.S. Pat. No. 6,207,446), ribosome display (See, e.g., Mattheakis et al. (1994) *Proc. Natl. Acad. Sci. USA* 91:9022 and Hanes et al. (2000) *Nat Biotechnol.* 18:1287-92; Hanes et al. (2000) *Methods Enzymol.* 328:404-30; and Schaffitzel et al. (1999) *J Immunol Methods.* 231(1-2):119-35), and *E. coli* periplasmic display (*J Immunol Methods.* 2005 Nov. 22; PMID: 16337958).

After display library members are isolated for binding to the target PEG antigen, each isolated library member can be also tested for its ability to bind to a non-target molecule to evaluate its binding specificity. Examples of non-target molecules include streptavidin on magnetic beads, blocking agents such as bovine serum albumin, non-fat bovine milk, soy protein, any capturing or target immobilizing monoclonal antibody, or non-transfected cells which do not express the target, or PEG molecules having a molecular weight very different from the PEG antigen used for antibody screening. A high-throughput ELISA screen can be used to obtain the data, for example. The ELISA screen can also be used to obtain quantitative data for binding of each library member to the target PEG antigen. The non-target and target binding data are compared (e.g., using a computer and software) to identify library members that specifically bind to the target.

After selecting candidate library members that bind to a target PEG antigen, each candidate library member can be further analyzed, e.g., to further characterize its binding properties for the target PEG antigen. Each candidate library member can be subjected to one or more secondary screening assays. The assay can be for a binding property, a catalytic property, an inhibitory property, a physiological property (e.g., cytotoxicity, renal clearance, immunogenicity), a structural property (e.g., stability, conformation, oligomerization state) or another functional property. The same assay can be used repeatedly, but with varying conditions, e.g., to determine pH, ionic, or thermal sensitivities.

As appropriate, the assays can use a display library member directly, a recombinant polypeptide produced from the nucleic acid encoding the selected polypeptide, or a synthetic peptide synthesized based on the sequence of the selected polypeptide. In the case of selected Fabs, the Fabs can be evaluated or can be modified and produced as intact IgG proteins. Exemplary assays for binding properties are described below.

Binding antibodies can also be evaluated using an ELISA assay. For example, each antibody candidate can be contacted to a microtitre plate whose bottom surface has been coated with the target PEG antigen, e.g., a limiting amount of the target. The plate is washed with buffer to remove non-specifically bound polypeptides. Then the amount of the binding antibody bound to the target on the plate is determined by probing the plate with an antibody that can recognize the binding antibody candidate, e.g., a tag or constant portion of the binding protein. The antibody is linked to a detection system (e.g., an enzyme such as alkaline phosphatase or horse radish peroxidase (HRP) which produces a colorimetric product when appropriate substrates are provided).

Alternatively, the ability of a binding antibody described herein to bind a target PEG antigen can be analyzed using a homogenous assay, i.e., after all components of the assay are added, additional fluid manipulations are not required. For example, fluorescence resonance energy transfer (FRET) can be used as a homogenous assay (see, for example, Lakowicz et al., U.S. Pat. No. 5,631,169; Stavrianopoulos, et al., U.S. Pat. No. 4,868,103). A fluorophore label on the first molecule (e.g., the molecule identified in the fraction) is selected such that its emitted fluorescent energy can be absorbed by a fluorescent label on a second molecule (e.g., the target) if the second molecule is in proximity to the first molecule. The fluorescent label on the second molecule fluoresces when it absorbs to the transferred energy. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. A binding event that is configured for monitoring by FRET can be conveniently measured through standard fluorometric detection means, e.g., using a fluorimeter. By titrating the amount of the first or second binding molecule, a binding curve can be generated to estimate the equilibrium binding constant.

Surface plasmon resonance (SPR) can be used to analyze the interaction of a binding protein and a target antigen. SPR or Biomolecular Interaction Analysis (BIA) detects biospecific interactions in real time, without labeling any of the interactants. Changes in the mass at the binding surface (indicative of a binding event) of the BIA chip result in alterations of the refractive index of light near the surface (the optical phenomenon of SPR). The changes in the refractivity generate a detectable signal, which are measured as an indication of real-time reactions between biological molecules. Methods for using SPR are described, for example, in U.S. Pat. No. 5,641,640; Raether, 1988, Surface Plasmons Springer Verlag; Sjolander and Urbaniczky, 1991, *Anal. Chem.* 63:2338-2345; Szabo et al., 1995, *Curr. Opin. Struct. Biol.* 5:699-705 and on-line resources provide by BIAcore International AB (Uppsala, Sweden).

Information from SPR can be used to provide an accurate and quantitative measure of the equilibrium dissociation constant ($K_D$), and kinetic parameters, including $K_{on}$ and $K_{off}$, for the binding of a binding protein to a target. Such data can be used to compare different biomolecules. For example, selected proteins from an expression library can be compared to identify proteins that have high affinity for the target or that have a slow $K_{off}$. This information can also be used to develop structure-activity relationships (SAR). For example, the kinetic and equilibrium binding parameters of matured versions of a parent protein can be compared to the parameters of the parent protein. Variant amino acids at given positions can be identified that correlate with particular binding parameters, e.g., high affinity and slow $K_{off}$. This information can be combined with structural modeling (e.g., using homology modeling, energy minimization, or structure determination by x-ray crystallography or NMR). As a result, an understanding of the physical interaction between the protein and its target can be formulated and used to guide other design processes.

As a further example, cellular assays may be used. Binding proteins can be screened for ability to bind to cells which transiently or stably express and display the target PEG on the cell surface. For example, anti-PEG antibodies can be fluorescently labeled and binding to PEG in the presence or absence of antagonistic antibody can be detected by a change in fluorescence intensity using flow cytometry e.g., a FACS machine.

Antigen-binding fragments of an intact antibody (full-length antibody) can be prepared via routine methods. For example, F(ab')2 fragments can be produced by pepsin digestion of an antibody molecule, and Fab fragments that can be generated by reducing the disulfide bridges of F(ab')2 fragments.

Genetically engineered antibodies, such as humanized antibodies, chimeric antibodies, single-chain antibodies, and bi-specific antibodies, can be produced via, e.g., conventional recombinant technology.

Methods for constructing humanized antibodies are also well known in the art. See, e.g., Queen et al., Proc. Natl. Acad. Sci. USA, 86:10029-10033 (1989). In one example, variable regions of VH and VL of a parent non-human antibody are subjected to three-dimensional molecular modeling analysis following methods known in the art. Next, framework amino acid residues predicted to be important for the formation of the correct CDR structures are identified using the same molecular modeling analysis. In parallel, human VH and VL chains having amino acid sequences that are homologous to those of the parent non-human antibody are identified from any antibody gene database using the parent VH and VL sequences as search queries. Human VH and VL acceptor genes are then selected.

The CDR regions within the selected human acceptor genes can be replaced with the CDR regions from the parent non-human antibody or functional variants thereof. When necessary, residues within the framework regions of the parent chain that are predicted to be important in interacting with the CDR regions (see above description) can be used to substitute for the corresponding residues in the human acceptor genes.

Antibodies obtained following a method known in the art and described herein can be characterized using methods well known in the art.

In some examples, an anti-PEG antibody can be prepared by the conventional recombinant technology. Standard molecular biology techniques can be used to prepare the recombinant expression vector, transfect the host cells, select for transformants, culture the host cells and recovery of the antibodies from the culture medium. For example, some antibodies can be isolated by affinity chromatography with a Protein A or Protein G coupled matrix.

(iii) Drug Delivery System

The hydrogel-based drug delivery system described herein may have a suitable concentration of the anti-PEG antibody as relative to the amount of the biodegradable polymers. In some embodiments, the concentration of the antibody is about 0.1 to 10% (w/v), for example, about 0.5-5% (w/v), about 0.5-2% (w/v) or about 0.5-1.0% (w/v) in the hydrogel. In some examples, the antibody concentration is about 1% (w/v).

The term "about" or "approximately" as used herein means within an acceptable error range for the particular value as determined by one of ordinary skill in the art, which will depend in part on how the value is measured or determined, i.e., the limitations of the measurement system. For example, "about" can mean within an acceptable standard deviation, per the practice in the art. Alternatively, "about" can mean a range of up to ±20%, preferably up to ±10%, more preferably up to ±5%, and more preferably still up to ±1% of a given value. Alternatively, particularly with respect to biological systems or processes, the term can mean within an order of magnitude, preferably within 2-fold, of a value. Where particular values are described in the application and claims, unless otherwise stated, the term "about" is implicit and in this context means within an acceptable error range for the particular value.

In some instances, the drug delivery system comprises the anti-PEG antibody and the hydrogel at a suitable ratio. For example, the anti-PEG antibody and the hydrogel may be at a ratio from about 1:1 to 1:100 (w/v), such as from about 1:1 to 1:50 (w/v), from 1:1 to 1:20 (w/v), about 1:3 (w/v) to about 1:5 (w/v), such as about 1:3 (w/v), about 1:4 (w/v), or about 1:5 (w/v). In some embodiments, the anti-PEG antibody and the hydrogel can be at a ratio of about 1:4 (w/v). In some examples, the drug delivery system contains 0.1-10 µg antibody per µl hydrogel, for example, 0.1-5 µg antibody per µl hydrogel, 0.5-5 µg antibody per µl hydrogel, 0.2-2 µg antibody per µl hydrogel, 0.5-2 µg antibody per µl hydrogel, or 0.5-1 µg antibody per µl hydrogel.

Pharmaceutical Compositions and Methods of Delivering Therapeutic Agents to Heart The hydrogel-based drug delivery system can be mixed with a pharmaceutically acceptable carrier (excipient) to form a pharmaceutical composition for use in treating a heart disease. "Acceptable" means that the carrier must be compatible with the active ingredient of the composition (and preferably, capable of stabilizing the active ingredient) and not deleterious to the subject to be treated. Pharmaceutically acceptable excipients (carriers) including buffers, which are well known in the art. See, e.g., Remington: The Science and Practice of Pharmacy 20th Ed. (2000) Lippincott Williams and Wilkins, Ed. K. E. Hoover.

The pharmaceutical compositions to be used in the present methods can comprise pharmaceutically acceptable carriers, excipients, or stabilizers in the form of lyophilized formulations or aqueous solutions. (Remington: The Science and Practice of Pharmacy 20th Ed. (2000) Lippincott Williams and Wilkins, Ed. K. E. Hoover). Acceptable carriers, excipients, or stabilizers are nontoxic to recipients at the dosages and concentrations used, and may comprise buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The pharmaceutical compositions to be used for in vivo administration must be sterile. This is readily accomplished by, for example, filtration through sterile filtration membranes. Therapeutic antibody compositions are generally placed into a container having a sterile access port, for example, an intravenous solution bag or vial having a stopper pierceable by a hypodermic injection needle.

The pharmaceutical compositions described herein can be in unit dosage forms such as solutions or suspensions, for local administration.

To perform a method of delivering a therapeutic agent to heart using the drug delivery system described herein, a suitable amount of the drug delivery system can be administered to a subject in need of the treatment, e.g., via injection, at an area of heart where a heart condition (e.g., ischemia or myocardial infarction) occurs or is suspected of occurring. In some instances, about 0.5-5 ml (e.g., about 1-5 ml, about 1-3 ml, or about 1-2 ml) of the drug delivery system is given to a subject each time. A target therapeutic agent, which is conjugated with PEG (i.e., pegylated), can then be administered to the subject via, e.g., systemic administration. The anti-PEG antibody embedded in the drug delivery system would attract the pegylated therapeutic agent to locate to the desired heart area, thereby exerting its therapeutic effects at the damaged site.

Without being bound by theory, the hydrogel-based drug delivery system described herein, after being placed at a suitable heart area as also described herein, may keep the anti-PEG antibody at the desired location for a suitable period, for example, at least 1 day (e.g., 3 days, 5 days, 7 days, or 10 days) via encapsulating the antibody in the matrix structure of the hydrogel. A suitable retention time for a specific anti-PEG antibody at a heart site may be achieved by adjusting the type of the polymers used for making the hydrogel, the percentage of crosslinks of the polymer(s), the ratio between the antibody and the hydrogel/polymer, and/or the percentage of the antibody in the hydrogel, etc. When needed, multiple doses of the drug delivery system may be given to the subject at the same site or nearby sites so as to maintain a suitable local concentration of the antibody. Given the ability of the drug delivery system described herein to retain the embedded antibody as noted herein, frequent administrations of the drug delivery system with short intervals is not needed. For example, when multiple doses are needed, each dose of the drug delivery system may be administered at least 3-14 days after the preceding dose. In some examples, two consecutive doses may be given to the subject at least 3 day apart, at least 7 day apart, or at least 14 days apart. In some embodiments, only one dose of the drug delivery system would be needed.

One or more doses of the pegylated therapeutic agent may be given to the subject at least 2 hours after the administration of the drug delivery system, for example at least 4 hours, at least 8 hours, at least 12 hours, at least 24 hours, or at least 48 hours after the administration of the drug delivery system.

Exemplary peglyated therapeutic agents for treating a heart condition can be a peglyated growth factor, include, but are not limited to, an insulin-like growth factor, granulocyte-colony stimulating factor (G-CSF), erythropoietin, a vascular endothelial growth factor, a platelet-derived growth factor, a hepatocyte growth factor, a neuregulin, a neurotrophin, a fibroblast growth factor, a stromal cell-derived factor, a growth differentiation factor, a transforming growth factor, a glial cell-derived neurotrophic factor, a migration stimulating factor, and a macrophage stimulating factor. Examples include Mircera®, Pegylated Mechano Growth Factor (PEG-MGF), and Neulasta®.

In some instances, the therapeutic agent is conjugated with PEG having a high molecular weight, for example, >10,000 kDa, >15,000 kDa, >20,000 kDa, or >25,000 kDa. In other instances, the therapeutic agent is conjugated with PEG having a low molecular weight, for example, <8,000 kDa, <5,000 kDa, <3,000 kDa, <2,000 kDa, <1,000 kDa, or <500 kDa. An anti-PEG antibody capable of binding to PEG molecules having specific molecular weights can be selected based on the PEG size of the pegylated therapeutic agent to be used for treating the cardiovascular disorder.

As used herein, the term "subject" refers to any mammal. In a preferred embodiment, the subject is human. In some examples, the subject is a human patient suffering from or suspected of having a heart condition, for example, myocardial infarction or ischemia.

As used herein, the term "treating" refers to the application or administration of a composition including one or more active agents to a subject, who has a target disease or disorder, a symptom of the disease/disorder, or a predisposition toward the disease/disorder, with the purpose to cure, heal, alleviate, relieve, alter, remedy, ameliorate, improve, or affect the disorder, the symptom of the disease, or the predisposition toward the disease or disorder.

Alleviating a target disease/disorder includes delaying the development or progression of the disease, or reducing disease severity. Alleviating the disease does not necessarily require curative results. As used therein, "delaying" the development of a target disease or disorder means to defer, hinder, slow, retard, stabilize, and/or postpone progression of the disease. This delay can be of varying lengths of time, depending on the history of the disease and/or individuals being treated. A method that "delays" or alleviates the development of a disease, or delays the onset of the disease, is a method that reduces probability of developing one or more symptoms of the disease in a given time frame and/or reduces extent of the symptoms in a given time frame, when compared to not using the method. Such comparisons are typically based on clinical studies, using a number of subjects sufficient to give a statistically significant result.

"Development" or "progression" of a disease means initial manifestations and/or ensuing progression of the disease. Development of the disease can be detectable and assessed using standard clinical techniques as well known in the art. However, development also refers to progression that may be undetectable. For purpose of this disclosure, development or progression refers to the biological course of the symptoms. "Development" includes occurrence, recurrence, and onset. As used herein "onset" or "occurrence" of a target disease or disorder includes initial onset and/or recurrence.

Kits for Delivering Therapeutic Agents to Heart

The present disclosure also provides kits for use in alleviating or treating a heart disease/disorder. Such kits can include one or more containers comprising (i) any of the drug delivery systems described herein, and (ii) a pharmaceutical composition comprising a pegylated therapeutic agent for treating the heart disease and a pharmaceutically acceptable carrier. In some instances, the drug delivery system as described herein comprises an anti-PEG antibody specifically binds PEG molecules having the same or similar molecule weights as the PEG molecules in the pegylated therapeutic agent.

In some embodiments, the kit can comprise instructions for use in accordance with any of the methods described herein. The included instructions can comprise a description of administration of the drug delivery system and the pegylated therapeutic agent to treat, delay the onset, or alleviate a target disease as those described herein. The kit may further comprise a description of selecting an individual suitable for treatment based on identifying whether that individual has the target disease. In still other embodiments, the instructions comprise a description of administering the drug delivery system and the peglyated therapeutic agent to an individual at risk of the target disease.

The instructions relating to the use of the drug delivery system and the peglyated therapeutic agent generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, delaying the onset and/or alleviating a heart disease or disorder. Instructions may be provided for practicing any of the methods described herein.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle).

Kits may optionally provide additional components such as buffers and interpretive information. Normally, the kit comprises a container and a label or package insert(s) on or associated with the container. In some embodiments, the invention provides articles of manufacture comprising contents of the kits described above.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook, et al., 1989) Cold Spring Harbor Press; Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney, ed., 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds., 1993-8) J. Wiley and Sons; Methods in Enzymology (Academic Press, Inc.); Handbook of Experimental Immunology (D. M. Weir and C. C. Blackwell, eds.); Gene Transfer Vectors for Mammalian Cells (J. M. Miller and M. P. Calos, eds., 1987); Current Protocols in Molecular Biology (F. M. Ausubel, et al., eds., 1987); PCR: The Polymerase Chain Reaction, (Mullis, et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practical approach (D. Catty, ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds., Harwood Academic Publishers, 1995).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1: Binding of Anti-PEG Antibodies to PEG-Conjugated Agents

Either anti-PEG antibody or control IgM (5 µg/mL) in 0.1 M NaHCO3/Na2CO3 (pH 8.0) were coated on a 96-well ELISA microplate for 4 h at 37° C., and then at 4° C. overnight. 2% skim milk/PBS was used to block the plate for 2 h at room temperature and then washed with PBS three times. PEG-modified compounds, including PEG-Qd800s (Invitrogen), Lipo-Dox (TTY Biopharm, Taiwan), and PEG-G-CSF (Pegfilgrastim, (Neulasta, Amgen) or Creative Bioworks) were serial diluted in 2% skim milk/PBS to different concentrations and were incubated on the plate at room temperature for 2 h. After washing, the plate was incubated with detection antibody 3.3-biotin (5 µg/ml) for 1 hr, followed by 1 hr with HRP-conjugated streptavidin (0.5 µg/ml) at room temperature. The plate was then incubated with 200 µL ABTS solution (0.4 mg/mL 2,2'-azino-di(3-ethylbenzthiazoline-6-sulfonic acid), 0.003% H2O2, 100 mM phosphate citrate, pH 4.0) in the dark for 15 min at room temperature. The absorbance at 405 nm was measured using microplate reader.

Results from an ELISA-based binding assay showed that the anti-PEG antibodies successfully bound to the various PEG-conjugated agents tested.

Example 2: Delivery of PEG-Conjugated Agents to Heart

Mice were subjected to either sham surgery, or cardiac ischemia-reperfusion surgery, where the left anterior descending coronary artery was reversibly occluded for 45 minutes, followed by reperfusion. Immediately following surgery, sterile saline, 10 µl of 1% (w/v) HA hydrogel containing 0.5 µg/µl IgM control or anti-PEG antibody (AGP6) was injected into the ischemic border region. 30 minutes later, PEG-modified quantum dots (PEG-QD800) were administered systemically via tail vein injection in 10 µl saline. After 48 hours, animals were systemically perfused with 50 ml saline via the abdominal aorta, and hearts were collected and processed for frozen sectioning. Sections were stained for Troponin I to demarcate cardiomyocytes, and quantum dots were visible on the far red channel.

Figure 1:
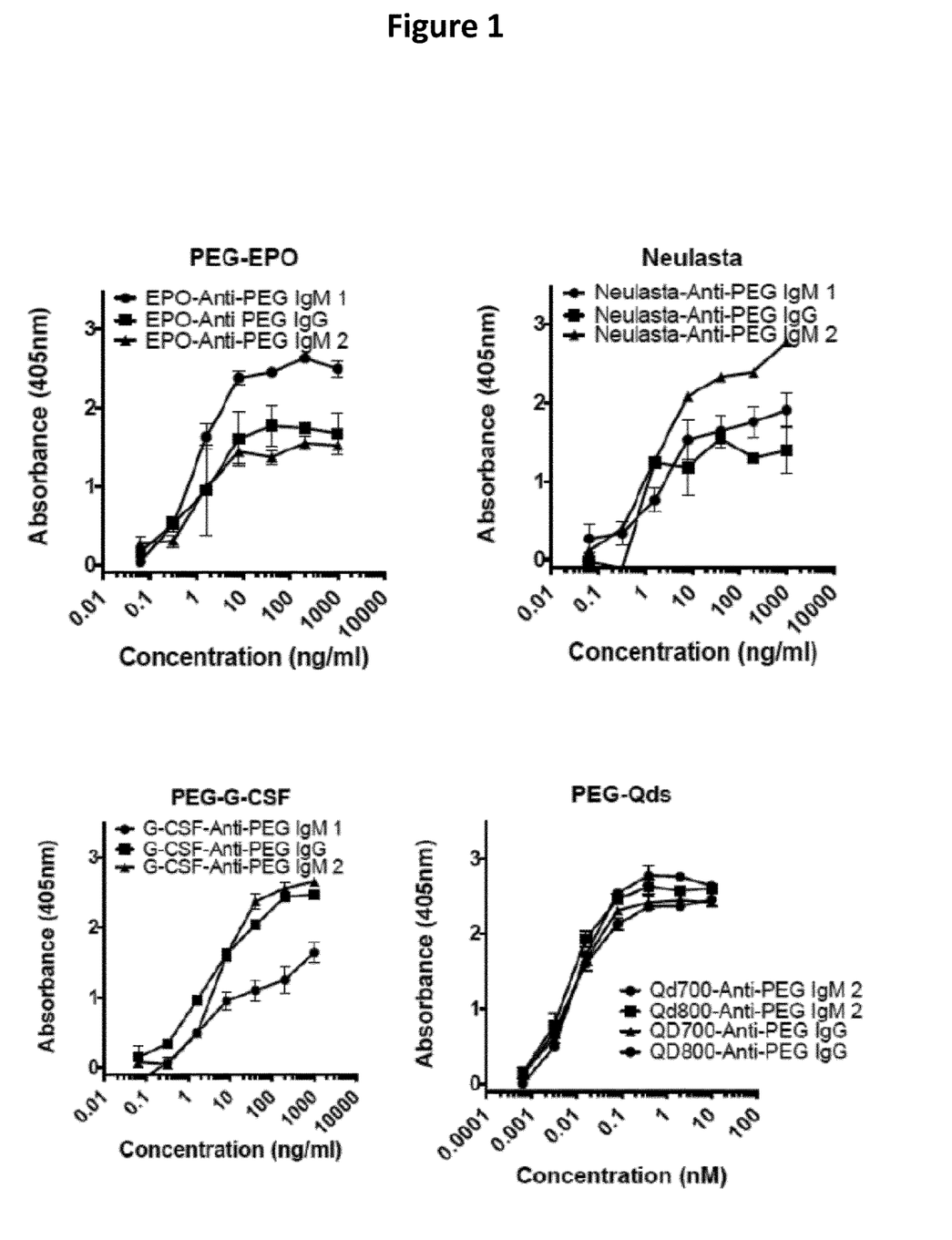
FIG. 1 includes charts showing that IgM and IgG anti-PEG antibodies are capable of binding a variety of PEG-modified compounds including PEG-modified erythropoietin (PEG-EPO), Neulasta, PEG-modified G-CSF, and PEG-modified quantum dots.
Figure 2:
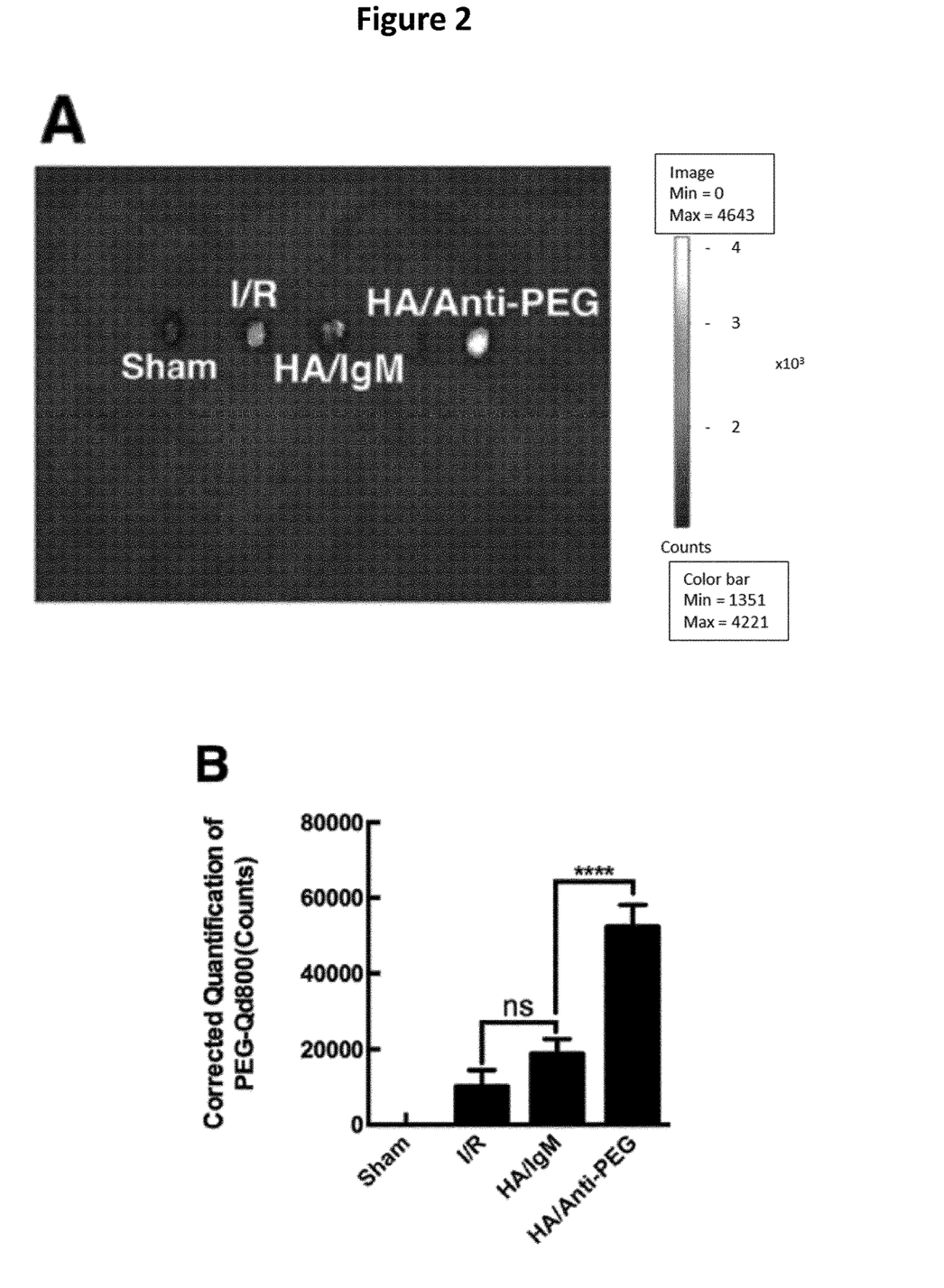
Figure 3:
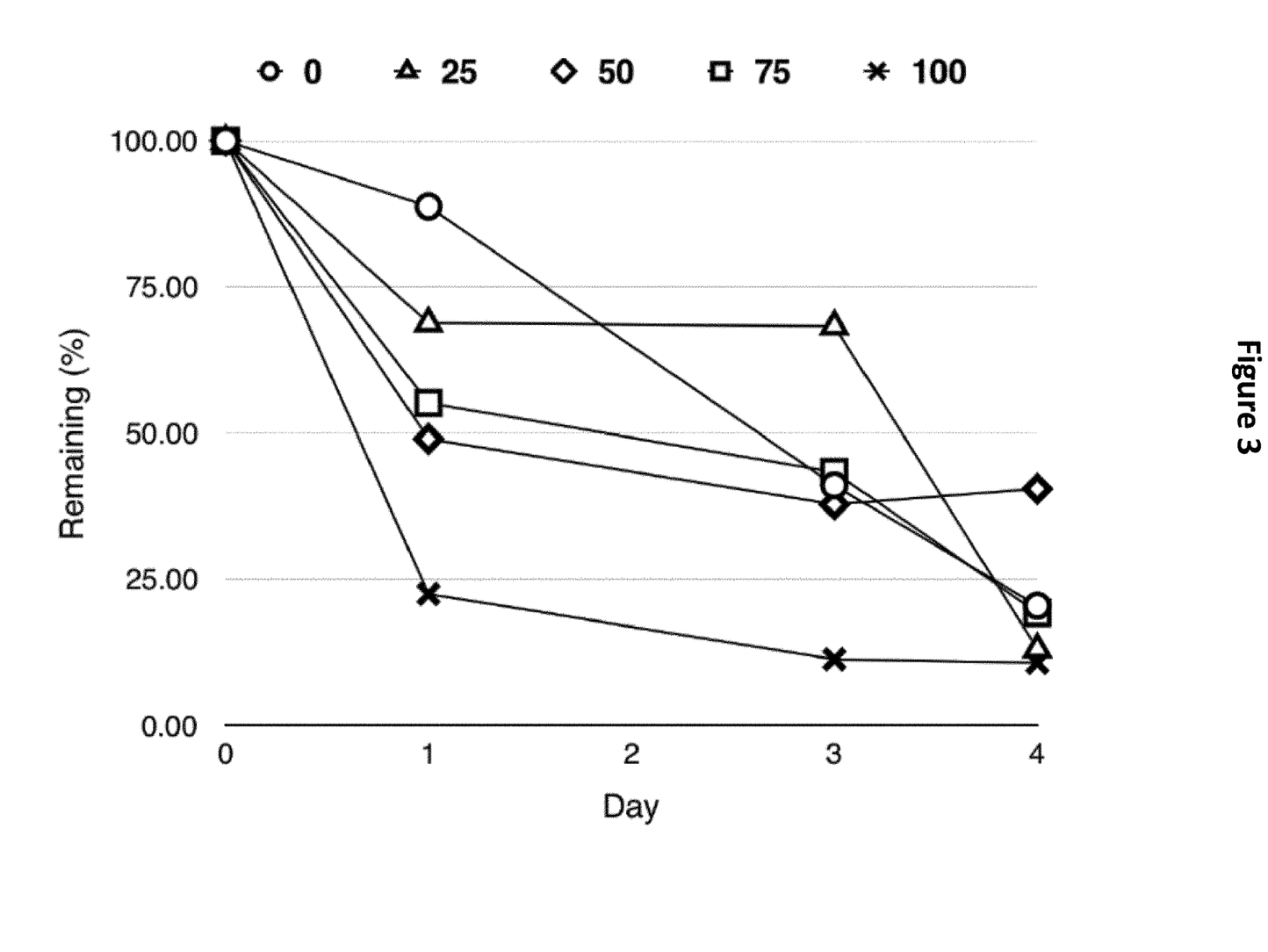
FIG. 3 is a chart showing the effect of HA cross-linking level on antibody retention rates.

As shown in FIG. 2, PEG-OD800 was detected in the ischemic region where the hydrogel containing the anti-PEG antibody was planted, indicating that PEG-conjugated agents were successfully delivered to heart by the drug delivery system described herein.

Example 3: Effect of Hyaluronic Acid Cross-Linking Level in Hydrogel on Antibody Retention Rates This study aims at investigating the effects of hyaluronic acid (HA) cross-linking levels of the HA-based hydrogels described herein on antibody retention rates. AlexaFluor®-conjugated IgM antibody (mouse) was suspended in hyaluronic acid (HA)-based hydrogels having 0%, 25%, 50%, 75%, or 100% HA cross-linking levels. The solutions were injected into the thigh muscle of FVB mice. The intensity of fluorescence at the injection site was quantified immediately following injection, then each day by the IVIS® Spectrum in vivo imaging system.

As shown in FIG. 5, hydrogels having higher HA cross-linking percentage (e.g., 100%) surprisingly showed lower antibody retention rate, while lower HA cross-linking percentage (e.g., 25% and 50%) showed higher antibody retention rate.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

The invention claimed is:

1. A drug delivery system for delivering a therapeutic agent to a heart, comprising an antibody embedded in a hydrogel, wherein the antibody is a IgG or IgM molecule that binds polyethylene glycol (PEG), wherein the hydrogel comprises one or more biodegradable polymers, and wherein 25% to 50% of the one or more biodegradable polymers contain inter-chain or intra-chain covalent cross-links.

2. The drug delivery system of claim 1, wherein the hydrogel comprises hyaluronic acid (HA) molecules.

3. The drug delivery system of claim 1, wherein the antibody is a human antibody or a humanized antibody.

4. The drug delivery system of claim 1, wherein the immunoglobulin molecule is an IgM molecule.

5. The drug delivery system of claim 1, wherein the amount of the antibody in the drug delivery system is 0.5-1% (w/v).

6. A kit for delivering a therapeutic agent to a heart, comprising:
   i. a drug delivery system set forth in claim 1; and
   ii. a therapeutic agent for treating a heart disease, wherein the therapeutic agent is conjugated to polyethylene glycol (PEG).

7. The kit of claim 6, wherein the therapeutic agent is a drug for treating an ischemic heart disease or myocardial infarction.

8. The kit of claim 6, wherein the therapeutic agent is a growth factor.

9. The kit of claim 8, wherein the growth factor is selected from the group consisting of an insulin-like growth factor, granulocyte-colony stimulating factor (G-CSF), erythropoietin, a vascular endothelial growth factor, a platelet-derived growth factor, a hepatocyte growth factor, a neuregulin, a neurotrophin, a fibroblast growth factor, a stromal cell-derived factor, a growth differentiation factor, a transforming growth factor, a glial cell-derived neurotrophic factor, a migration stimulating factor, and a macrophage stimulating factor.

10. A method for delivering a therapeutic agent to heart, comprising:
   i. administering to a subject having or at risk for a heart disorder a drug delivery system as set forth in claim 1, wherein the drug delivery system is placed at a heart area where the heart disorder occurs or is suspected to occur; and
   ii. administering systemically a therapeutic agent for treating the heart disorder, wherein the therapeutic agent is conjugated with polyethylene glycol (PEG).

11. The method of claim 10, wherein the heart disorder is heart ischemia or myocardial infarction.

12. The method of claim 10, wherein about 1-2 ml of the drug delivery system is administered to the subject each time.

13. The method of claim 10, wherein the drug delivery system is administered to the subject by multiple doses.

14. The method of claim 10, wherein the drug delivery system is administered to the subject only once.

15. The method of claim 10, wherein the therapeutic agent is a growth factor.

16. The method of claim 15, wherein the growth factor is selected from the group consisting of an insulin-like growth factor, granulocyte-colony stimulating factor (G-CSF), erythropoietin, a vascular endothelial growth factor, a platelet-derived growth factor, a hepatocyte growth factor, a neuregulin, a neurotrophin, a fibroblast growth factor, a stromal cell-derived factor, a growth differentiation factor, a transforming growth factor, a glial cell-derived neurotrophic factor, a migration stimulating factor, and a macrophage stimulating factor.

* * * * *